US009868090B2

(12) United States Patent
Ishikawa et al.

(10) Patent No.: US 9,868,090 B2
(45) Date of Patent: Jan. 16, 2018

(54) PROCESS FOR PREPARING CHEMICAL LIQUID OF SILYLATING AGENT AND SURFACE TREATMENT METHOD

(71) Applicant: TOKYO OHKA KOGYO CO., LTD., Kawasaki-shi (JP)

(72) Inventors: Kiyoshi Ishikawa, Kawasaki (JP); Akira Kumazawa, Kawasaki (JP); Daijiro Mori, Kawasaki (JP)

(73) Assignee: TOKYO OHKA KOGYO CO., LTD., Kawasaki-shi (JP)

( * ) Notice: Subject to any disclaimer, the term of this patent is extended or adjusted under 35 U.S.C. 154(b) by 0 days.

(21) Appl. No.: 15/070,806

(22) Filed: Mar. 15, 2016

(65) Prior Publication Data
US 2016/0279578 A1 Sep. 29, 2016

(30) Foreign Application Priority Data

Mar. 24, 2015 (JP) ................. 2015-060985

(51) Int. Cl.
*C23G 1/00* (2006.01)
*B01D 69/02* (2006.01)
*B01D 15/36* (2006.01)
*C07F 7/10* (2006.01)
*B01D 61/14* (2006.01)
*B01D 61/20* (2006.01)
*B01D 61/02* (2006.01)

(52) U.S. Cl.
CPC .......... *B01D 69/02* (2013.01); *B01D 15/361* (2013.01); *C07F 7/10* (2013.01); *B01D 61/02* (2013.01); *B01D 61/14* (2013.01); *B01D 61/145* (2013.01); *B01D 61/147* (2013.01); *B01D 61/20* (2013.01); *B01D 2311/2623* (2013.01); *B01D 2325/42* (2013.01)

(58) Field of Classification Search
CPC .... B01D 61/14; B01D 61/145; B01D 61/147; B01D 61/20; B01D 2311/2623; B01D 2311/2626; B01D 69/02; B24B 57/00; B24B 57/02; B01J 39/02; B01J 39/04; B01J 39/043; B01J 39/046
See application file for complete search history.

(56) References Cited

U.S. PATENT DOCUMENTS

| | | | | |
|---|---|---|---|---|
| 2,884,384 A * | 4/1959 | Howell, Jr. | ............... | B01J 49/50 208/263 |
| 3,658,729 A * | 4/1972 | De Pree | ................... | B01J 49/53 210/674 |
| 3,663,163 A * | 5/1972 | De Pree | ................... | B01J 49/53 210/672 |
| 5,292,439 A * | 3/1994 | Morita | ..................... | B01J 41/14 210/638 |
| 5,330,735 A * | 7/1994 | Cronin | .................. | C01B 7/0706 210/670 |
| 5,397,477 A * | 3/1995 | Salem | ....................... | C02F 1/42 210/683 |
| 5,762,829 A * | 6/1998 | Deshpande | ........... | C01B 33/166 252/62 |
| 5,876,685 A * | 3/1999 | Krulik | ..................... | C01B 7/191 203/41 |
| 6,471,871 B1 * | 10/2002 | Pitzer | ..................... | C02F 1/5236 205/502 |
| 8,029,623 B2 * | 10/2011 | Geissler | ................. | B01J 41/043 134/10 |
| 2006/0037912 A1 * | 2/2006 | Wertsching | .............. | B01J 39/04 210/681 |
| 2009/0199460 A1 * | 8/2009 | Munson | ................. | B01D 15/00 44/308 |
| 2009/0311874 A1 | 12/2009 | Tomita et al. | | |

FOREIGN PATENT DOCUMENTS

JP       2010-114414       5/2010

* cited by examiner

Primary Examiner — Sharidan Carrillo
(74) Attorney, Agent, or Firm — Knobbe Martens Olson & Bear LLP

(57) ABSTRACT

A process removes metal impurities from an untreated chemical liquid, which includes a silylating agent. The process includes providing a strongly acidic cation-exchange resin in which a cation-exchange group is immobilized to a resin membrane or an integral structure of a particle-removing membrane and an ion exchange resin membrane in which a strongly acidic cation-exchange resin has been chemically introduced onto surfaces of pores in a porous resin. The wettability of the ion exchange resin membrane is thereafter improved by contacting the ion-exchange resin membrane with an organic solvent. The metal impurities are then removed from the untreated chemical liquid by passing the untreated chemical liquid through the ion-exchange resin membrane.

15 Claims, No Drawings

PROCESS FOR PREPARING CHEMICAL LIQUID OF SILYLATING AGENT AND SURFACE TREATMENT METHOD

This application claims priority to Japanese Patent Application No. 2015-060985, filed on Mar. 24, 2015, the content of which is incorporated herein by reference.

BACKGROUND OF THE INVENTION

Field of the Invention

The present invention relates to a process for preparing a chemical liquid of a silylating agent and a surface treatment method.

Related Art

Recently, there is an increasing tendency that semiconductor devices are highly integrated and have a finer pattern, and thus, the miniaturization and high aspect ratio of the pattern is progressing. However, meanwhile, there is a problem such as a so-called pattern collapse. The pattern collapse is a phenomenon that when many patterns are formed in parallel on the substrate, the adjacent patterns are so close that they lean against each other, and thus, in some cases, the patterns are broken from the base part. If such pattern collapse occurs, the desired product cannot be obtained and therefore the yield and reliability of the product are decreased.

The "pattern" used herein includes both of a "resist pattern" to be formed on a substrate by a lithography process (light exposure and developing processes) as a semiconductor manufacturing process and an "inorganic pattern" to be formed by an etching process of the substrate after the lithography process. The modification method on the surface of the substrate according to the present invention is effective for the treatment of the "inorganic pattern" among these patterns.

It is believed that the pattern collapse is caused by the surface tension of the rinse liquid when the rinse liquid is dried off in the rinsing treatment by pure water or the like after the pattern is formed. In other words, at the time of removing the rinse liquid in the drying process, the stress between the patterns based on the surface tension of the rinse liquid is affected, and thus, pattern collapse is caused.

Accordingly, if the surface of the pattern can be hydrophobized to enhance a contact angle of a rinsing liquid, a force applied to between patterns in a drying process after rinsing can be reduced, making it possible to prevent pattern collapse. Furthermore, the larger aspect ratio of the pattern increases the force applied to between the patterns, and tends to improve the effect of suppressing pattern collapse by means of hydrophobization.

Accordingly, a surface treatment method has been adopted of exposing a substrate surface to a chemical liquid of a silylating agent to render the surface water-repellent or hydrophobic (for example, Patent Document 1).
Patent Document 1: Japanese Unexamined Patent Application, Publication No. 2010-114414

SUMMARY OF THE INVENTION

As with cleaning liquids for wafer cleaning, chemical liquids of silylating agent should contain little or no metal impurities, which are likely to increase junction leakage current of devices, and should be clean. However, some of chemical liquids of silylating agent are likely to be heat-deteriorated or hydrolyzed, and may therefore not be purified by distillation.

The present invention has been made in view of the above problems, and an object of the present invention is to provide a process for preparing a chemical liquid of a silylating agent that has a reduced content of metal impurities, and a surface treatment method using a chemical liquid of a silylating agent obtained by such a preparation method.

According to a first aspect of the present invention, there is provided a process for preparing a chemical liquid of a silylating agent, the process comprising: reducing metal impurities contained in an untreated chemical liquid of a silylating agent, using an ion-exchange resin membrane that has been brought into contact with an organic solvent in advance.

According to a second aspect of the present invention, there is provided a surface treatment method that hydrophobizes a substrate surface, the method comprising: exposing the substrate surface to a chemical liquid of a silylating agent obtained by the process for preparing a chemical liquid of a silylating agent according to the first aspect of the present invention.

The present invention provides a process for preparing a chemical liquid of a silylating agent that has a reduced content of metal impurities and a surface treatment method using a chemical liquid of a silylating agent obtained by the preparation process.

DETAILED DESCRIPTION OF THE INVENTION

<<Process for Preparing Chemical Liquid of Silylating Agent>>

The process for preparing a chemical liquid of a silylating agent in the present embodiment includes a step of reducing metal impurities contained in an untreated chemical liquid of a silylating agent using an ion-exchange resin membrane that has been brought into contact with an organic solvent in advance (hereinafter also referred to as "metal-impurity reduction step"). Specifically, the metal-impurity reduction step includes passing an untreated chemical liquid of a silylating agent into an ion-exchange resin membrane that has been brought into contact with an organic solvent in advance, more specifically (1) a step of bringing an ion-exchange resin membrane into contact with an organic solvent in advance and (2) a step of passing an untreated chemical liquid of a silylating agent into the ion-exchange resin membrane.

The expression "untreated chemical liquid of silylating agent" as used herein means a chemical liquid before passage into the ion-exchange resin membrane that has been brought into contact with an organic solvent in advance. The untreated chemical liquid of the silylating agent is a liquid containing a silylating agent and metal impurities, for example, it may be a liquid that further contains an organic solvent. In general, however, the chemical liquid of the silylating agent before treatment may be, for example, a liquid that is not necessary to contain an organic solvent and contains only a silylating agent in addition to impurities or may be a liquid containing only a silylating agent and metal impurities.

[Ion-Exchange Resin Membrane]

The ion-exchange resin membrane used in the present embodiment is not particularly limited, and filters including an ion-exchange resin comprising a suitable ion-exchange group immobilized to a resin membrane may be used. Examples of such ion-exchange resin membranes include strongly acidic cation-exchange resins comprising a cation-exchange group such as a sulfonic acid group chemically modified on a high-density polyethylene membrane and ion-exchange resin membranes with a particle-removing membrane that is a membrane having an integral structure of a particle-removing membrane and an ion-exchange resin membrane, the ion-exchange resin membranes with a particle-removing membrane having been manufactured by a strongly acidic cation-exchange resin chemically introduced into the surface of pores in a porous high-density polyethylene medium. Polyalkylene membranes with an ion-exchange group chemically modified thereon are preferred. Polyalkylenes include, for example, polyethylene and polypropylene, and polypropylene is preferred. Cation-exchange groups are preferred as the ion-exchange group. Ion-exchange resin membranes used in the present embodiment may be commercially available products as filters for metal ion removal.

In the process for preparing a chemical liquid of a silylating agent in the present embodiment, the ion-exchange resin membrane is brought into contact with an organic solvent in advance. There is a commercially available product in a dry state of the ion-exchange resin membrane. Further, there is also a hydrophilic material having a high level of affinity for aqueous solutions. In the present embodiment, even when such ion-exchange resin membranes are used, preliminary contact with an organic solvent can allow metal impurities in the untreated chemical liquid of the silylating agent to be effectively removed and the reduction effect is significantly superior to the case of the ion-exchange resin membrane having not been brought into contact with the organic solvent in advance.

[Organic Solvent]

In the present embodiment, an organic solvent to be brought into contact with the ion-exchange resin membrane in advance is preferably an organic solvent not containing a functional group reactive with the silylating agent. Either a single kind or a mixture of two or more kinds of organic solvent may be used.

Specific examples of preferred organic solvents to be brought into contact with the ion-exchange resin membrane in advance in the present embodiment include sulfoxides such as dimethylsulfoxide; sulfones such as dimethylsulfone, diethylsulfone, bis(2-hydroxyethyl)sulfone, and tetramethylenesulfone; amides such as N,N-dimethylformamide, N-methylformamide, N,N-dimethylacetamide, N-methylacetamide, and N,N-diethylacetamide; lactams such as N-methyl-2-pyrrolidone, N-ethyl-2-pyrrolidone, N-propyl-2-pyrrolidone, N-hydroxymethyl-2-pyrrolidone, and N-hydroxyethyl-2-pyrrolidone; imidazolidinones such as 1,3-dimethyl-2-imidazolidinone, 1,3-diethyl-2-imidazolidinone, and 1,3-diisopropyl-2-imidazolidinone; dialkyl glycol ethers such as dimethyl glycol, dimethyl diglycol, dimethyl triglycol, methylethyl diglycol, and diethyl glycol; (poly)alkylene glycol monoalkyl ethers such as ethylene glycol monomethyl ether, ethylene glycol monoethyl ether, ethylene glycol mono-n-propyl ether, ethylene glycol mono-n-butyl ether, diethylene glycol monomethyl ether, diethylene glycol monoethyl ether, diethylene glycol mono-n-propyl ether, diethylene glycol mono-n-butyl ether, triethylene glycol monomethyl ether, triethylene glycol monoethyl ether, propylene glycol monomethyl ether, propylene glycol monoethyl ether, propylene glycol mono-n-propyl ether, propylene glycol mono-n-butyl ether, dipropylene glycol monomethyl ether, dipropylene glycol monoethyl ether, dipropylene glycol mono-n-propyl ether, dipropylene glycol mono-n-butyl ether, tripropylene glycol monomethyl ether, and tripropylene glycol monoethyl ether; (poly)alkylene glycol monoalkyl ether acetates such as ethylene glycol monomethyl ether acetate, ethylene glycol monoethyl ether acetate, diethylene glycol monomethyl ether acetate, diethylene glycol monoethyl ether acetate, propylene glycol monomethyl ether acetate, and propylene glycol monoethyl ether acetate; ethers such as dimethyl ether, diethyl ether, methylethyl ether, dipropyl ether, diisopropyl ether, dibutyl ether, diisoamyl ether, diethylene glycoldimethyl ether, diethylene glycolmethylethyl ether, diethylene glycoldiethyl ether, and tetrahydrofuran; ketones such as methylethyl ketone, cyclohexanone, 2-heptanone, and 3-heptanone; lactic acid alkyl esters such as methyl 2-hydroxypropionate and ethyl 2-hydroxypropionate; esters such as ethyl 2-hydroxy-2-methylpropionate, methyl 3-methoxypropionate, ethyl 3-methoxypropionate, methyl 3-ethoxypropionate, ethyl 3-ethoxypropionate, ethyl ethoxyacetate, ethyl hydroxyacetate, methyl 2-hydroxy-3-methylbutanoate, 3-methyl-3-methoxybutyl acetate, 3-methyl-3-methoxybutyl propionate, ethyl acetate, n-propyl acetate, i-propyl acetate, n-butyl acetate, i-butyl acetate, n-pentyl formate, i-pentyl acetate, n-butyl propionate, ethyl butyrate, n-propyl butyrate, i-propyl butyrate, n-butyl butyrate, methyl pyrubate, ethyl pyrubate, n-propyl pyrubate, methyl acetoacetate, ethyl acetoacetate, and ethyl 2-oxobutanoate; lactones such as β-propylolactone, γ-butyrolactone, and 5-pentylolactone; linear, branched, or cyclic hydrocarbons such as n-hexane, n-heptane, n-octane, n-nonane, methyloctane, n-decane, n-undecane, n-dodecane, 2,2,4,6,6-pentamethylheptane, 2,2,4,4,6,8,8-heptamethylnonane, cyclohexane, and methylcyclohexane; aromatic hydrocarbons such as benzene, toluene, naphthalene, and 1,3,5-trimethylbenzene; and terpenes such as p-menthane, diphenylmenthane, limonene, terpinene, bornane, norbornane, and pinane. These solvents may be used solely or as a mixture of two or more of them. Among them, propylene glycol monomethyl ether acetate (PE-MEA); linear, branched, or cyclic hydrocarbons; and terpenes such as p-menthane, diphenylmenthane, limonene, terpinene, bornane, norbornane, and pinane are preferred.

[Step of Bringing Ion-Exchange Resin Membrane into Contact with Organic Solvent in Advance]

In the metal-impurity reduction step in the present embodiment, specifically, the ion-exchange resin membrane is brought into contact with an organic solvent prior to passage of the untreated chemical liquid of the silylating agent into the ion-exchange resin membrane.

Any method for bringing the ion-exchange resin membrane into contact with the organic solvent may be used without particular limitation, and examples thereof include: a method in which the organic solvent is passed into the ion-exchange resin membrane; and a method in which the ion-exchange resin membrane is immersed in the organic solvent. A method in which, while immersing the ion-exchange resin membrane in the organic solvent, the organic solvent is passed little by little through the ion-exchange resin membrane is preferred. Specifically, this method is carried out by feeding the organic solvent into a filtering device with the ion-exchange resin membrane installed therein. In this case, the organic solvent can be passed little by little through the ion-exchange resin membrane while immersing the ion-exchange resin membrane in the organic solvent by pouring the organic solvent in such an amount that the ion-exchange resin membrane is immersed in the organic solvent.

The ion-exchange resin membrane is contacted with the organic solvent, for example, for one min or more, preferably 10 min or more, more preferably 20 min or more. The upper limit of the contact time is not particularly limited.

From the viewpoint of production efficiency, however, the contact time is, for example, 2 hr or less, preferably one hr or less, more preferably 40 min or less.

In the process for preparing a chemical liquid of a silylating agent in the present embodiment, the wettability of the ion-exchange resin membrane can be improved by bringing the ion-exchange resin membrane into contact with an organic solvent in advance. Therefore, the untreated chemical liquid of the silylating agent to be passed through the ion-exchange resin membrane in a later step can easily be permeated into pores present within the ion-exchange resin membrane, and the concentration of metal impurities contained in the untreated chemical liquid of the silylating agent can be significantly reduced. Further, even when the ion-exchange resin membrane contains water, the water can be removed.

The silylating agent is generally likely to be polymerized as a result of a reaction with water, and thus, the content of water in the reaction process is preferably reduced in advance. To this end, preferably, purging with nitrogen is carried out prior to the contact of the ion-exchange resin membrane with the organic solvent, and the organic solvent is brought into contact with the ion-exchange resin membrane under a closed environment such as a glove box purged with nitrogen.

[Step of Passing Untreated Chemical Liquid of Silylating Agent into Ion-Exchange Resin Membrane]

In the present embodiment, after bringing the ion-exchange resin membrane into contact with the organic solvent, the untreated chemical liquid of a silylating agent is passed through the ion-exchange resin membrane. Any method of passage may be used without particular limitation. For example, the passage can be carried out by feeding the untreated chemical liquid of the silylating agent into a filtering device with the ion-exchange resin membrane installed therein. From the viewpoint of production efficiency, the step of bringing the ion-exchange resin membrane into contact with the organic solvent using the filtering device can be followed by the step of passage using the same filtering device.

Conditions for preliminary contact of the ion-exchange resin membrane with the organic solvent followed by passage of the untreated chemical liquid of the silylating agent through the ion-exchange resin membrane are not particularly limited, and the flow rate may be, for example, 10 to 400 ml/min, preferably 100 to 300 ml/min, more preferably 150 to 250 ml/min.

[Untreated Chemical Liquid of a Silylating Agent]

As described above, the untreated chemical liquid of the silylating agent used in the present embodiment is a liquid that contains at least the silylating agent and metal impurities. The "untreated chemical liquid of silylating agent" as used herein is a term that aims to be distinguished from a chemical liquid of a silylating agent after treatment (hereinafter referred to also as "treated chemical liquid of silylating agent) that flows out from the ion-exchange resin membrane after passage of the chemical liquid of a silylating agent through the ion-exchange resin membrane in the metal-impurity reduction step in the present embodiment. It is needless to say that the silylating agent contained in the untreated chemical liquid of the silylating agent may be the same as that contained in the treated chemical liquid of the silylating agent.

[Silylating Agent]

The type of the silylating agent is not particularly limited as long as the silylating agent can hydrophobize the substrate surface, and the silylating agent can be properly selected from silylating agents that have hitherto been used to render various materials water-repellent or hydrophobic. The "hydrophobization" as used herein is a concept including water repelling. Silylating agents that can be employed in the present embodiment will be described.

Silylating agents used for hydrophobization of the substrate surface are not particularly limited as long as a desired hydrophobizing effect on the substrate surface can be attained. The silylating agent to be used may be properly selected from silylating agents that have hitherto been used as hydrophobilizing agents for various materials.

The silylating agent contained in the chemical liquid of the silylating agent may be, for example, a silicon compound represented by the following general formula (1).

$(R^1)_a Si(H)_b X^1_{4-a-b}$ (1)

wherein each $R^1$ independently represents a monovalent organic group containing a monovalent hydrocarbon group having 1 to 18 carbon atoms in which a part or all of hydrogen atoms may be substituted by a fluorine atom; each $X^{1'}$ represents a monovalent functional group having nitrogen that is an atom bonded to the silicon atom; a is an integer of 1 to 3; and b is an integer of 0 to 2, with the total of a and b being 1 to 3.

Examples of the preferred silylating agent may include silylating agents represented by the following General Formulas (3) to (10) or a cyclic silazane compound. Hereinafter, the silylating agents represented by General Formulas (3) to (10) and the cyclic silazane compound will be described in order.

(Silylating Agent Represented by General Formula (3))

(3)

In General Formula (3), each of $R^1$, $R^2$, and $R^3$ independently represents a hydrogen atom, a halogen atom, or an organic group. The sum of the carbon atoms of the $R^1$, $R^2$, and $R^3$ is 1 or more. $R^4$ represents a hydrogen atom or a saturated or unsaturated chain hydrocarbon group. $R^5$ represents a hydrogen atom, a saturated or unsaturated chain hydrocarbon group, a saturated or unsaturated non-aromatic cyclic hydrocarbon group, or a non-aromatic heterocyclic group. $R^4$ and $R^5$ may be connected to each other to form non-aromatic heterocycles having a nitrogen atom.

In the case of $R^1$, $R^2$, and $R^3$ being halogen atoms, a chlorine atom, a bromine atom, an iodine atom, and a fluorine atom are preferable.

In the case of $R^1$, $R^2$, and $R^3$ being organic groups, the organic groups may include hetero atoms in addition to a carbon atom. The type of the hetero atom that may be included in the organic group is not particularly limited within the range that the purpose of the present invention is not negatively affected. The hetero atoms that may be included in the organic groups are preferably N, O, and S. In the case of $R^1$, $R^2$, and $R^3$ being organic groups, the sum of the number of the carbon atoms and the number of the hetero atoms which are included in the organic groups is not particularly limited as long as the sum of the carbon number of the $R^1$, $R^2$, and $R^3$ is 1 or more. In the case of $R^1$, $R^2$, and $R^3$ being organic groups, the sum of the number of the carbon atoms and the number of the hetero atoms which are included in the organic groups is preferably 1 to 10, more preferably 1 to 8, and still more preferably 1 to 3. In the case of $R^1$, $R^2$, and $R^3$ being organic groups, a saturated or unsaturated chain hydrocarbon group, an aralkyl group, and an aromatic hydrocarbon group are preferable as the organic groups. Preferred examples of the saturated or unsaturated chain hydrocarbon group may include a methyl group, an ethyl group, a vinyl group, an n-propyl group, an isopropyl group, an allyl group, a 1-propenyl group, an isopropenyl group, an n-butyl group, a sec-butyl group, a tert-butyl group, a 3-butenyl group, an n-pentyl group, an isopentyl group, a sec-pentyl group, a tert-pentyl group, an n-hexyl group, an n-heptyl group, an n-octyl group, an n-nonyl group and an n-decyl group. Among these chain hydrocarbon groups, a methyl group, an ethyl group, a vinyl group, an n-propyl group, and an allyl group are more preferable, and a methyl group, an ethyl group, and a vinyl group are still more preferable. Preferred examples of the aralkyl group may include a benzyl group, a phenyl ethyl group, a phenyl propyl group, an α-naphthyl methyl group and a β-naphthyl methyl group. Preferred examples of the aromatic hydrocarbon group may include a phenyl group, an α-naphthyl group, and a β-naphthyl group.

In the case of $R^4$ being a saturated or unsaturated chain hydrocarbon group, the carbon number of the saturated or unsaturated chain hydrocarbon group is not particularly limited within the range that the purpose of the present invention is not negatively affected. In the case of $R^4$ being a saturated or unsaturated chain hydrocarbon group, the carbon number of the saturated or unsaturated chain hydrocarbon group is preferably 1 to 10, more preferably 1 to 8, and still more preferably 1 to 3. Preferred examples of $R^4$ being a saturated or unsaturated chain hydrocarbon group are the same as saturated or unsaturated chain hydrocarbon groups exemplified as preferred groups for $R^1$, $R^2$, and $R^3$.

In the case of $R^5$ being a saturated or unsaturated chain hydrocarbon group, the saturated or unsaturated chain hydrocarbon group is the same as $R^4$. In the case of $R^5$ being a saturated or unsaturated cyclic hydrocarbon group, the carbon number of the saturated or unsaturated cyclic hydrocarbon group is not particularly limited within the range that the purpose of the present invention is not negatively affected. In the case of $R^5$ being a saturated or unsaturated non-aromatic cyclic hydrocarbon group, the carbon number of the saturated or unsaturated non-aromatic cyclic hydrocarbon group is preferably 3 to 10, more preferably 3 to 6, and still more preferably 5 or 6. Preferred examples of $R^5$ being a saturated or cyclic hydrocarbon group include a cyclopropyl group, a cyclobutyl group, a cyclopentyl group, a cyclohexyl group, a cyclopentyl group, and a cyclooctyl group. In the case of $R^5$ being a non-aromatic heterocyclic group, the hetero atom included in the non-aromatic heterocyclic group is not particularly limited within the range that the purpose of the present invention is not negatively affected. In the case of $R^5$ being a non-aromatic heterocyclic group, preferred examples of the hetero atom included in the non-aromatic heterocyclic group may include N, O, and S. In the case of $R^5$ being a non-aromatic heterocyclic group, the sum of the number of the hetero atoms and the number of the carbon atoms included in the non-aromatic heterocyclic group is not particularly limited within the range that the purpose of the present invention is not negatively affected. In the case of $R^5$ being a non-aromatic heterocyclic group, the sum of the number of the hetero atoms and the number of the carbon atoms included in the non-aromatic heterocyclic group is preferably 3 to 10, more preferably 3 to 6, and still more preferably 5 or 6. Preferred examples of $R^5$ being a non-aromatic heterocyclic group include a pyrrolidin-1-yl group, a piperidine-1-yl group, a piperazine-1-yl group, a morpholine-1-yl group, and a thiomorpholine-1-yl group.

The number of the atoms included in the non-aromatic heterocyclic group that is formed by binding $R^4$ and $R^5$ to each other is not particularly limited within the range that the purpose of the present invention is not negatively affected. The non-aromatic heterocyclic group that is formed by binding $R^4$ and $R^5$ to each other is preferably a 3-membered ring to a 10-membered ring and more preferably a 5-membered ring or a 6-membered ring. The type of other hetero atom of the carbon atom included in the non-aromatic heterocyclic group that is formed by binding $R^4$ and $R^5$ to each other is not particularly limited within the range that the purpose of the present invention is not negatively affected. A preferred hetero atom included in the non-aromatic heterocyclic group that is formed by binding $R^4$ and $R^5$ to each other may be N, O, and S. Preferred examples of the non-aromatic heterocyclic group that is formed by binding $R^4$ and $R^5$ to each other may include pyrrolidine, piperidine, piperazine, morpholine and thiomorpholine.

Specific examples of a silylating agent represented by General Formula (3) may include N,N-dimethylamino trimethyl silane, N,N-dimethylamino dimethyl silane, N,N-dimethylamino monomethyl silane, N,N-diethylamino trimethyl silane, t-butyl amino trimethyl silane, allyl amino trimethyl silane, trimethylsilyl acetamide, N,N-dimethylamino dimethyl vinyl silane, N,N-dimethylamino dimethyl propyl silane, N,N-dimethylamino dimethyl octyl silane, N,N-dimethylamino dimethyl phenylethyl silane, N,N-dimethylamino dimethyl phenyl silane, N,N-dimethylamino dimethyl-t-butyl silane, N,N-dimethylamino triethyl silane and trimethyl silanamine.

(Silylating Agent Represented by General Formula (4))

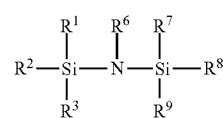

(4)

In General Formula (4), $R^1$, $R^2$, and $R^3$ are the same as in the above General Formula (3). $R^6$ represents a hydrogen atom, a methyl group, a trimethyl silyl group, or a dimethyl silyl group. Each of $R^7$, $R^8$, and $R^9$ independently represents a hydrogen atom or an organic group. The sum of the carbon numbers of $R^7$, $R^8$, and $R^9$ is 1 or more.

In the case of $R^7$, $R^8$, and $R^9$ being organic groups, the organic groups are the same as in the case of $R^1$, $R^2$, and $R^3$ being organic groups.

Specific examples of the silylating agent represented by General Formula (4) include hexamethyldisilazane, N-methyl hexamethyldisilazane, 1,1,3,3-tetramethyl disilazane, 1,3-dimethyl disilazane, 1,3-di-n-octyl-1,1,3,3-tetramethyl disilazane, 1,3-divinyl-1,1,3,3,-tetramethyl disilazane, tris(dimethyl silyl)amine, tris(trimethylsilyl)amine, 1-ethyl-1,1,3,3,3-pentamethyl disilazane, 1-vinyl-1,1,3,3,3-pentamethyl disilazane, 1-propyl-1,1,3,3,3-pentamethyl disilazane, 1-phenylethyl-1,1,3,3,3-pentamethyl disilazane, 1-tert-butyl-1,1,3,3,3-pentamethyl disilazane, 1-phenyl-1,1,3,3,3-pentamethyl disilazane and 1,1,1-trimethyl-3,3,3-triethyl disilazane.

(Silylating Agent Represented by General Formula (5))

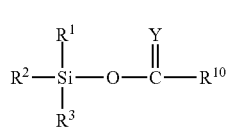

(5)

In General Formula (5), $R^1$, $R^2$, and $R^3$ are the same as in the above General Formula (3). Y represents O, $CHR^{11}$, $CHOR^{11}$, $CR^{11}R^{11}$, or $NR^{12}$. Each of $R^{10}$ and $R^{11}$ independently represents a hydrogen atom, a saturated or unsaturated chain hydrocarbon group, a saturated or unsaturated non-aromatic cyclic hydrocarbon group, a trialkyl silyl group, a trialkyl siloxy group, an alkoxy group, a phenyl group, a phenyl ethyl group, or an acetyl group. $R^{12}$ represents a hydrogen atom, an alkyl group, or a trialkyl silyl group.

In the case of $R^{10}$ and $R^{11}$ being saturated or unsaturated chain hydrocarbon groups or saturated or unsaturated non-aromatic cyclic hydrocarbon groups, the saturated or unsaturated chain hydrocarbon groups or saturated or unsaturated non-aromatic cyclic hydrocarbon groups are the same as in the case of $R^5$ being a saturated or unsaturated chain hydrocarbon group or a saturated or unsaturated non-aromatic cyclic hydrocarbon group in General Formula (3).

In the case of $R^{10}$ and $R^{11}$ being trialkyl silyl groups, a trialkyl slioxy or alkoxy groups, the carbon number of the alkyl groups included therein is not particularly limited as long as the purpose of the present invention is not negatively affected. The carbon number of the alkyl group included therein is preferably 1 to 10, more preferably 1 to 8, and still more preferably 1 to 3. Preferred examples of the alkyl group included therein may include a methyl group, an ethyl group, an n-propyl group, an isopropyl group, an n-butyl group, a sec-butyl group, a tert-butyl group, an n-pentyl group, an isopentyl group, a sec-pentyl group, a tert-pentyl group, an n-hexyl group, an n-heptyl group, an n-octyl group, an n-nonyl group and an n-decyl group. Among these alkyl groups, a methyl group, an ethyl group, and an n-propyl group are more preferable, and a methyl group and an ethyl group are still more preferable.

In the case of $R^{12}$ being an alkyl group or a trialkyl silyl group, the carbon number of the alkyl groups included in an alkyl group or a trialkyl silyl group is not particularly limited within the range that the purpose of the present invention is not negatively affected. The carbon number of the alkyl group included in an alkyl group or a trialkyl silyl group is preferably 1 to 10, more preferably 1 to 8, and still more preferably 1 to 3. Preferred examples of the alkyl group included in an alkyl group or a trialkyl silyl group may include a methyl group, an ethyl group, an n-propyl group, an isopropyl group, an n-butyl group, a sec-butyl group, a tert-butyl group, an n-pentyl group, an isopentyl group, a sec-pentyl group, a tert-pentyl group, an n-hexyl group, an n-heptyl group, an n-octyl group, an n-nonyl group and an n-decyl group. Among these alkyl groups, a methyl group, an ethyl group, and an n-propyl group are more preferable, and a methyl group and an ethyl group are still more preferable.

Specific examples of the silylating agent represented by General Formula (5) may include trimethylsilyl acetate, dimethylsilyl acetate, monomethylsilyl acetate, trimethylsilyl propionate, trimethylsilyl butylate and trimethylsilyl-2-butenoate.

(Silylating Agent Represented by General Formula (6))

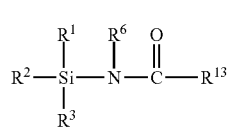

(6)

In General Formula (6), $R^1$, $R^2$, and $R^3$ are the same as in the above General Formula (3). $R^6$ is the same as the above General Formula (4). $R^{13}$ represents a hydrogen atom, a saturated or unsaturated chain hydrocarbon group, a trifluoromethyl group, or a trialkylsilyl amino group.

In the case of $R^{13}$ being a saturated or unsaturated chain hydrocarbon group, the saturated or unsaturated chain hydrocarbon group is the same as the case of $R^4$ being a saturated or unsaturated chain hydrocarbon group in General Formula (3).

In the case of $R^{13}$ being a trialkylsilyl amino group, the alkyl group included in the trialkylsilyl amino group is the same as the alkyl group included therein in the case of $R^{10}$ and $R^{11}$ being trialkyl silyl groups, trialkyl siloxy groups, or alkoxy groups in General Formula (5).

Specific examples of the silylating agent represented by General Formula (6) may include N,N'-bis(trimethylsilyl) urea, N-trimethylsilyl acetamide, N-methyl-N-trimethylsilyl trifluoro acetamide and N,N-bis(trimethylsilyl)trifluoro acetamide.

(Silylating Agent Represented by General Formula (7))

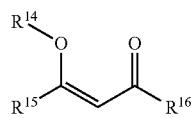

(7)

In General Formula (7), $R^{14}$ represents a trialkyl silyl group. Each of $R^{15}$ and $R^{16}$ independently represents a hydrogen atom or an organic group.

In the case of $R^{14}$ being a trialkyl silyl group, the alkyl group included in the trialkyl silyl group is the same as the alkyl group included therein in the case of $R^{10}$ and $R^{11}$ being trialkyl silyl groups, trialkyl siloxy groups, or alkoxy groups in General Formula (5).

In the case of $R^{15}$ and $R^{16}$ being organic groups, the organic groups are the same as the organic groups in the case of $R^1$, $R^2$, and $R^3$ being organic groups in General Formula (3).

Specific examples of the silylating agent represented by General Formula (7) may include 2-trimethylsiloxypentane-2-ene-4-one.

(Silylating Agent Represented by General Formula (8))

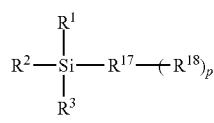

(8)

In General Formula (8), $R^1$, $R^2$, and $R^3$ are the same as in the above General Formula (3). $R^{17}$ represents a saturated or unsaturated chain hydrocarbon group, a saturated or unsaturated non-aromatic cyclic hydrocarbon group, or a non-aromatic heterocyclic group. $R^{18}$ represents $-SiR^1R^2R^3$. p represents 0 or 1.

When p is 0, the saturated or unsaturated chain hydrocarbon group, saturated or unsaturated non-aromatic cyclic hydrocarbon group, or non-aromatic heterocyclic group as $R^{17}$ is the same as $R^5$ in General Formula (3). When p is 1, the organic group as $R^{17}$ is a divalent group in which one hydrogen atom is excluded from the organic group in the case of $R^1$, $R^2$, and $R^3$ being organic groups in General Formula (3).

Specific examples of the silylating agent represented by General Formula (8) may include 1,2-bis(dimethyl chlorosilyl)ethane and t-butyldimethyl chlorosilane.

(Silylating Agent Represented by General Formula (9))

$$R^{19}{}_q Si[N(CH_3)_2]_{4-q} \qquad (9)$$

In General Formula (9), each $R^{19}$ independently represents a chain hydrocarbon group having 1 to 18 carbon atoms in which some or all of the hydrogen atoms may be substituted by fluorine atoms. q is 1 or 2.

In General Formula (9), the number of carbon atoms of $R^{19}$ is preferably 2 to 18 and more preferably 8 to 18.

Examples of $R^{19}$ being a chain saturated hydrocarbon group with no substitution by fluorine atoms include a methyl group, an ethyl group, an n-propyl group, an isopropyl group, a butyl group, a sec-butyl group, a tert-butyl group, an isobutyl group, an amyl group, an isoamyl group, a tert-amyl group, a hexyl group, a 2-hexyl group, a 3-hexyl group, a heptyl group, a 2-heptyl group, a 3-heptyl group, an isoheptyl group, a tert-heptyl group, an n-octyl group, an isooctyl group, a tert-octyl group, a 2-ethyl hexyl group, a nonyl group, an isononyl group, a decyl group, a dodecyl group, an tridecyl group, a tetradecyl group, a pentadecyl group, a hexadecyl group, a heptadecyl group and an octadecyl group.

Examples of $R^{19}$ being a chain unsaturated hydrocarbon group with no substitution by fluorine atoms include a vinyl group, a 1-propenyl group, an allyl group, an isopropenyl group, a 1-butenyl group, a 2-butenyl group, a 3-butenyl group, a 1,3-butadienyl group, a 1-ethyl vinyl group, a 1-methyl-1-propenyl group, a 1-methyl-2-propenyl group, a 4-pentenyl group, a 1,3-pentadienyl group, a 2,4-pentadienyl group, a 3-methyl-1-butenyl group, a 5-hexenyl group, a 2,4-hexadienyl group, a 6-heptenyl group, a 7-octenyl group, an 8-nonenyl group, a 9-decenyl group, a 10-undecenyl group, a 11-dodecenyl group, a 12-tridecenyl group, a 13-tetradecenyl group, a 14-pentadecenyl group, a 15-hexadecenyl group, a 16-heptadecenyl group, a 17-octadecenyl group, an ethynyl group, a propargyl group, a 1-propynyl group, a 1-butynyl group, a 2-butynyl group, a 3-butynyl group, a 1-pentynyl group, a 2-pentynyl group, a 3-pentynyl group, a 4-pentynyl group, a 1-hexynyl group, a 2-hexynyl group, a 3-hexynyl group, a 4-hexynyl group, a 5-hexynyl group, a 6-heptynyl group, a 7-octynyl group, a 8-nonynyl group, a 9-decynyl group, a 10-undecynyl group, a 11-dodecynyl group, a 12-tridecynyl group, a 13-tetradecynyl group, a 14-pentadecynyl group, a 15-hexadecynyl group, a 16-heptadecynyl group and a 17-octadecynyl group.

In the case of $R^{19}$ being a chain hydrocarbon group with no substitution by fluorine atoms, the number and site of the substitution of the fluorine atom are not particularly limited. The number of the substitution of the fluorine atom in the chain hydrocarbon group is preferably 50% or more, more preferably 70% or more, and still more preferably 80% or more of the number of the hydrogen atoms included in the chain hydrocarbon group.

$R^{19}$ is preferably a linear hydrocarbon group in which some or all of the hydrogen atoms may be substituted by a fluorine atom, because an excellent hydrophobization effect can easily be attained. In addition, $R^{19}$ is preferably a saturated linear chain hydrocarbon group having 1 to 18 carbon atoms (an alkyl group having 1 to 18 carbon atoms), in which some or all of the hydrogen atoms may be substituted by a fluorine atom, from the viewpoint of the storage stability of the silylating agent.

In General Formula (9), q is 1 or 2, and preferably 1.

(Silylating Agent Represented by General Formula (10))

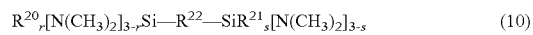

$$R^{20}{}_r[N(CH_3)_2]_{3-r}Si-R^{22}-SiR^{21}{}_s[N(CH_3)_2]_{3-s} \qquad (10)$$

In General Formula (10), each of $R^{20}$ and $R^{21}$ independently represents a hydrogen atom, or a linear chain or branched alkyl group having 1 to 4 carbon atoms. $R^{22}$ represents a linear chain or branched alkylene group having 1 to 16 carbon atoms. r and s are independently integers of 0 to 2.

$R^{20}$ and $R^{21}$ may be the same as or different to each other. $R^{20}$ and $R^{21}$ are preferably a hydrogen atom or a linear chain or branched alkyl group having 1 to 3 carbon atoms, more preferably a hydrogen atom or a methyl group, and still more preferably a methyl group.

Specific examples of $R^{20}$ and $R^{21}$ being linear chain or branched alkyl groups having 1 to 4 carbon atoms include a methyl group, an ethyl group, an n-propyl group, an isopropyl group, an n-butyl group, a sec-butyl group, a tert-butyl group and an isobutyl group.

The compound represented by General Formula (10) includes a linear chain or branched alkylene group having 1 to 16 carbon atoms as $R^{22}$. The linear chain or branched alkylene group as $R^{22}$ has preferably 1 to 10 carbon atoms, and more preferably 2 to 8 carbon atoms. In addition, the linear chain alkylene group is a methylene group or an α,ω-linear chain alkylene group, and the branched alkylene group is a methylene group and an alkylene group other than an α,ω-linear chain alkylene group. $R^{22}$ is preferably the linear chain alkylene group.

Examples of $R^{22}$ being a linear chain or branched alkylene group having 1 to 16 carbon atoms include a methylene group, a 1,2-ethylene group, a 1,1-ethylene group, a propane-1,3-diyl group, a propane-1,2-diyl group, a propane-1,1-diyl group, a propane-2,2-diyl group, a butane-1,4-diyl group, a butane-1,3-diyl group, a butane-1,2-diyl group, a butane-1,1-diyl group, a butane-2,2-diyl group, a butane-2,3-diyl group, a pentane-1,5-diyl group, a pentane-1,4-diyl group, a hexane-1,6-diyl group, a heptane-1,7-diyl group, an octane-1,8-diyl group, a 2-ethyl hexane-1,6-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group and a hexadecane-1,16-diyl group.

In the compound represented by General Formula (10), s and r are independently integers of 0 to 2. Since the synthesis and obtaining of the compound represented by Formula (10) are easy, s and r are preferably 1 or 2, and more preferably 2.

(Cyclic Silazane Compound)

As a silylating agent, a cyclic silazane compound is also preferable. Hereinafter, the cyclic silazane compound will be described.

Examples of the cyclic silazane compound may include cyclic disilazane compounds such as 2,2,5,5-tetramethyl-2,5-disila-1-azacyclopentane and 2,2,6,6-tetramethyl-2,6-disila-1-azacyclohexane; cyclic trisilazane compounds such as 2,2,4,4,6,6-hexamethylcyclotrisilazane and 2,4,6-trimethyl-2,4,6-trivinylcyclotrisilazane; cyclic tetrasilazane compounds such as 2,2,4,4,6,6,8,8-octamethylcyclotetrasilazane; and the like.

Among them, the cyclic disilazane compounds are preferable, and 2,2,5,5-tetramethyl-2,5-disila-1-azacyclopentane and 2,2,6,6-tetramethyl-2,6-disila-1-azacyclohexane are more preferable. As the cyclic disilazane compounds, there is a 5-membered ring structure such as 2,2,5,5-tetramethyl-2,5-disila-1-azacyclopentane and a 6-membered ring structure such as 2,2,6,6-tetramethyl-2,6-disila-1-azacyclohexane, but the 5-membered ring structure is more preferable.

[Metal Impurities]

Metal impurities contained in the untreated chemical liquid of the silylating agent in an embodiment of the present invention are not particularly limited, and, for example, metal impurities containing at least one metal element selected from the group consisting of group 4, group 5, group 6, group 7, group 8, group 9, and group 10 metal elements may be mentioned. Among them, at least one metal element selected from the group consisting of Fe, Cu, Al, Zn, Co, Li, Na, K, Ca, Cr, Mn, Pb, Ni, Ru, Rh, Pd, Re, Os, Ir, Pt, W, and Mo is preferred as the metal element. In particular, at least one metal element selected from the group consisting of Fe, Cu, Al, and Zn is more preferred because they can easily be removed from the untreated chemical liquid of the silylating agent by the process for preparing a chemical liquid of a silylating agent in the present embodiment. These metal impurities may be simple substances of metal elements. The "containing metal element" as used herein means a simple substance of the metal element or a metal compound containing the metal element. This is true of the case where the "metal element" is a specific metal element such as "Al element."

[Other Ingredients]

The untreated chemical liquid of the silylating agent used in the present embodiment may contain ingredients other than the above silylating agent and metal impurities as long as the purpose of the present invention is not negatively affected.

Other ingredients are not particularly limited, and examples thereof include organic solvents. When the silylating agent is not a liquid, the incorporation of an organic solvent is preferred. However, if the substrate surface can be exposed to the silylating agent, there is no need to contain the organic solvent. When the organic solvent is contained, it is needless to say that the organic solvent contained in the untreated chemical liquid of the silylating agent may be the same as the organic solvent contained in the treated chemical liquid of the silylating agent.

The organic solvent that may be contained in the untreated chemical liquid of the silylating agent is not particularly limited but is preferably an organic solvent that is of the same type as the organic solvent that is brought into contact with the ion-exchange resin membrane in advance in the present embodiment.

[Treated Chemical Liquid of Silylating Agent]

In the present embodiment, the chemical liquid of a silylating agent obtained in the metal-impurity reduction step (treated chemical liquid of the silylating agent) has a lower metal-impurity concentration than that in the untreated chemical liquid of the silylating agent.

As described above, the chemical liquid of the silylating agent (treated chemical liquid of the silylating agent) obtained in the process for preparing the chemical liquid of the silylating agent in the present embodiment has a lowered metal-impurity concentration and thus is suitable as a treating liquid for a substrate surface and particularly suitable as a treating liquid for the surface of a substrate for use, for example, in the manufacture of semiconductor devices.

<<Surface Treatment Method>>

A surface treatment method comprising exposing, to a substrate surface, a chemical liquid of a silylating agent obtained by the process for preparing a chemical liquid of a silylating agent in a first aspect of the present invention to hydrophobilize the substrate surface is also in the scope of the present invention. In this surface treatment method, the chemical liquid of the silylating agent can be used as the treating liquid for the substrate surface.

The material for the substrate is not particularly limited and may be selected from various inorganic substrates and organic substrates and determined depending upon the type of the silylating agent to be used. The substrate surface is not particularly limited and may be subjected to surface modification treatment, for example, by conventional publicly known methods.

Any conventional publicly known methods can be used as the method for exposing, to the substrate surface, the chemical liquid of the silylating agent without particular limitation. Examples thereof include a method in which the silylating agent is vaporized to produce vapor that is then brought into contact with a substrate surface and a method in which a substrate surface treating liquid containing a silylating agent is brought into contact with the substrate surface, for example, by spray coating, spin coating, dip coating, or roll coating.

Among the above methods, the method in which the substrate surface treating liquid containing a silylating agent is brought into contact with a substrate surface is preferred because the substrate surface can easily be evenly treated.

In the present embodiment, preferably, when the organic solvent or the like contained in the chemical liquid of the silylating agent stays on the substrate surface after exposure of the chemical liquid of the silylating agent to the substrate surface, the residue is removed. Any method may be used for the removal of the residue without particular limitation, and examples thereof include a method in which gas such as nitrogen or dry air is sprayed on the substrate surface, and a method in which the substrate is heated to a suitable temperature depending upon the boiling point of the solvent to be removed.

In the surface treatment method in the present embodiment, a film (a thin film) containing a silicon compound can be formed on a substrate surface by dehydrocondensation between hydroxyl groups produced by hydrolysis of the silylating agent and for the film, the substrate surface can be hydrophobized.

Since the substrate surface can be hydrophobized by the surface treatment method in the present embodiment, for example, for a substrate having a surface with fine patterns formed herein, pattern collapse can be suppressed by hydrophobization of the substrate surface.

EXAMPLES

Hereinafter, the present invention will be described in more detail with reference to Examples, but the present invention is not limited to these Examples.

Examples 1,2

Trimethylsilyldimethylamine (TMSDMA) was provided as a silylating agent, and a liquid consisting of 100% of TMSDMA was used as an untreated chemical liquid of a silylating agent. An ion-exchange resin membrane (DFA1SRPESW44; manufactured by PALL) was installed in a filtering device, and, in a glove box purged with nitrogen (i.e., in nitrogen), was immersed in propylene glycol monomethyl ether acetate (PGMEA). Thereafter, an untreated chemical liquid of a silylating agent was passed through the ion-exchange resin membrane at a flow rate of about 200 ml/min, and a procedure of taking 100 ml of a sample, each time when 1000 ml of the chemical liquid was filtered through the membrane, was repeated three times. The amount of metal impurities contained in the untreated chemical liquid of the silylating agent and the amount of metal impurities contained in the three sample liquids were measured by ICP-MS, and the three measured values were averaged. This measurement was carried out twice.

Comparative Example 1

The amount of metal impurities was measured in the same manner as in Example 1, except that the ion-exchange resin membrane had not been brought into contact with PGMEA in advance.

[Measurement of Residual Ratio of Metal Impurities]

As with Examples and Comparative Example, the amount of metal impurities in the untreated silylating agent was measured, and the residual ratio of metal impurities represented by a value of B/A in percentage terms was determined, where A represents the amount of metal impurities contained in the untreated chemical liquid of silylating agent; and B represents the amount of metal impurities contained in the treated chemical liquid of the silylating agent obtained in the metal-impurity reduction step. The results are shown in Table 1.

TABLE 1

|  | Al | Cu | Zn |
|---|---|---|---|
| Example 1 | 51.8 | 32.9 | 4.3 |
| Example 2 | 49.7 | 17.8 | 1.5 |
| Comparative Example 1 | 69.3 | 68.8 | 38.6 |

Numerical values in Table 1 are in %.

As is apparent from Table 1, in Example 1 where the ion-exchange resin membrane had been brought into contact with PGMEA in advance, the residual ratio of metal impurities represented by a value of B/A in percentage terms, where A represents the amount of metal impurities contained in the untreated chemical liquid of silylating agent and B represents the amount of metal impurities contained in the treated chemical liquid of the silylating agent obtained in the metal-impurity reduction step, was 23 to 42.4% for Cu, 45.6 to 63.5% for Al, and 4.15 to 4.35% for Zn, indicating that the concentration of metal impurities was reduced and the degree of the reduction was significantly superior to that in Comparative Example 1 where the ion-exchange resin membrane had not been brought into contact with PGMEA in advance.

It was found that, also for Example 2 where the used amount of the untreated chemical liquid of the silylating agent was increased by a factor of four, the concentration of metal impurities was reduced to substantially the same degree as that in Example 1.

What is claimed is:

1. A process for preparing a chemical liquid comprising a silylating agent, the process comprising sequential steps of:
    contacting an ion-exchange resin membrane with an organic solvent; and
    removing metal impurities from an untreated chemical liquid comprising the silylating agent by passing the untreated chemical liquid through the ion-exchange resin membrane, thereby obtaining the chemical liquid,
    wherein the organic solvent is alkylene glycol alkyl ether acetate.

2. The process according to claim 1, wherein the metal impurities include at least one metal selected from the group consisting of Fe, Cu, Al, and Zn.

3. The process according to claim 1, wherein the ion-exchange resin membrane is purged with nitrogen before the contact with the organic solvent.

4. The process according to claim 1, wherein the alkylene glycol alkyl ether acetate is propylene glycol monomethyl ether acetate (PGMEA).

5. The process according to claim 1, wherein the silylating agent is a silicon compound represented by the following general formula (1):

$$(R^1)_a Si(H)_b X^1_{4-a-b} \qquad (1)$$

wherein each $R^1$ independently represents a monovalent organic group comprising a monovalent hydrocarbon group having 1 to 18 carbon atoms in which a part or all of hydrogen atoms may be substituted by fluorine atoms; each $X^1$ independently represents a monovalent functional group having nitrogen that is an atom bonded to the silicon atom; a is an integer of 1 to 3; and b is an integer of 0 to 2, with the total of a and b being 1 to 3.

6. The process according to claim 1, wherein the untreated chemical liquid consists of the silylating agent and the metal impurities.

7. A process for treating a substrate surface, the process comprising:
    obtaining a chemical liquid comprising a silylating agent by the process according to claim 1; and
    exposing the substrate surface to the chemical liquid.

8. The process according to claim 1, wherein the ion exchange resin membrane comprises a filter including an ion-exchange resin.

9. The process according to claim 1, wherein the ion exchange resin membrane is selected from the group consisting of a strongly acidic cation-exchange resin comprising a cation-exchange group immobilized to a resin membrane and an integral structure of a particle-removing membrane and an ion exchange resin membrane in which a strongly acidic cation-exchange resin has been chemically introduced onto surfaces of pores in a porous resin.

10. A process for preparing a chemical liquid comprising a silylating agent, the process comprising sequential steps of:
    contacting an ion-exchange resin membrane with an organic solvent; and
    removing metal impurities from an untreated chemical liquid comprising a silylating agent by passing the untreated chemical liquid through the ion-exchange resin membrane, thereby obtaining the chemical liquid,
    wherein the ion-exchange resin membrane is purged with nitrogen before contacting with the organic solvent.

11. The process according to claim 10, wherein the ion exchange resin membrane is selected from the group consisting of a strongly acidic cation-exchange resin comprising a cation-exchange group immobilized to a resin membrane and an integral structure of a particle-removing membrane and an ion exchange resin membrane in which a strongly acidic cation-exchange resin has been chemically introduced onto surfaces of pores in a porous resin.

12. A process for preparing a chemical liquid comprising a silylating agent, the process comprising sequential steps of:
    contacting an ion-exchange resin membrane with an organic solvent; and
    removing metal impurities from an untreated chemical liquid comprising a silylating agent by passing the untreated chemical liquid through the ion-exchange resin membrane, thereby obtaining the chemical liquid, wherein the silylating agent is a silicon compound represented by the following general formula (1) respectively:

wherein each $R^1$ independently represents a monovalent organic group comprising a monovalent hydrocarbon group having 1 to 18 carbon atoms in which a part or all of hydrogen atoms may be substituted by fluorine atoms; each $X^1$ independently represents a monovalent functional group having nitrogen that is an atom bonded to the silicon atom; a is an integer of 1 to 3; and b is an integer of 0 to 2, with the total of a and b being 1 to 3.

13. The process according to claim 12, wherein the ion exchange resin membrane is selected from the group consisting of a strongly acidic cation-exchange resin comprising a cation-exchange group immobilized to a resin membrane and an integral structure of a particle-removing membrane and an ion exchange resin membrane in which a strongly acidic cation-exchange resin has been chemically introduced onto surfaces of pores in a porous resin.

14. The process according to claim 12, wherein the silylating agent comprises trimethylsilyldimethylamine (TMSDMA).

15. A process for treating a substrate surface, the process comprising:
    obtaining a chemical liquid comprising a silylating agent by the process according to claim 12; and
    exposing the substrate surface to the chemical liquid.

* * * * *